(12) United States Patent
Truitt et al.

(10) Patent No.: US 7,134,434 B2
(45) Date of Patent: *Nov. 14, 2006

(54) PRESSURE SUPPORT SYSTEM AND METHOD AND A PRESSURE CONTROL VALVE FOR USE IN SUCH A SYSTEM AND METHOD

(75) Inventors: Patrick W Truitt, Murrysville, PA (US); Richard J Lordo, Pittsburgh, PA (US); Joseph J Gesner, Trafford, PA (US)

(73) Assignee: RIC Investments, LLC, Wilmington, DE (US)

( * ) Notice: Subject to any disclaimer, the term of this patent is extended or adjusted under 35 U.S.C. 154(b) by 529 days.

This patent is subject to a terminal disclaimer.

(21) Appl. No.: 10/647,497

(22) Filed: Aug. 25, 2003

(65) Prior Publication Data

US 2004/0035422 A1 Feb. 26, 2004

Related U.S. Application Data

(63) Continuation of application No. 09/347,071, filed on Jul. 2, 1999, now Pat. No. 6,615,831.

(51) Int. Cl.
*A61M 16/00* (2006.01)
*A62B 7/00* (2006.01)

(52) U.S. Cl. ............ 128/204.18; 128/204.21; 128/204.23; 128/204.24; 128/205.25; 128/201.28; 128/206.15; 128/200.24; 128/204.22; 128/207.12; 128/207.16; 128/204.19; 128/205.24; 137/498; 137/625.65; 251/905

(58) Field of Classification Search ............ 128/204.18, 128/204.21, 204.23, 204.24, 205.25, 201.28, 128/206.15, 200.24, 204.22, 207.12, 207.16, 128/204.19, 205.24; 137/498, 625.65; 251/905
See application file for complete search history.

(56) References Cited

U.S. PATENT DOCUMENTS

| 2,996,078 | A | | 8/1961 | Freeman et al. |
| 3,811,431 | A | | 5/1974 | Apstein |
| 3,811,531 | A | | 5/1974 | Forssman |
| 4,207,884 | A | * | 6/1980 | Isaacson ................ 128/200.24 |
| 4,336,590 | A | * | 6/1982 | Jacq et al. ............. 128/204.21 |
| 4,524,947 | A | | 6/1985 | Barnes et al. |
| 4,726,366 | A | * | 2/1988 | Apple et al. ........... 128/204.21 |
| 4,957,107 | A | | 9/1990 | Sipin |
| 4,967,781 | A | | 11/1990 | Baron |
| 5,020,771 | A | | 6/1991 | Nakatsukasa et al. |
| 5,127,400 | A | * | 7/1992 | DeVries et al. ........ 128/205.24 |
| 5,230,330 | A | * | 7/1993 | Price ..................... 128/203.11 |
| 5,237,987 | A | | 8/1993 | Anderson et al. |

(Continued)

*Primary Examiner*—Henry Bennett
*Assistant Examiner*—Nihir Patel
(74) *Attorney, Agent, or Firm*—Michael W. Haas

(57) ABSTRACT

A pressure support system having enhanced noise reduction and a valve assembly for use in pressure support system. The pressure support system includes a pressure generator having an inlet and an outlet. A first conduit defining a tortuous path is coupled between a gas source and the inlet of the pressure generator. A second conduit coupled to the outlet of the pressure generator delivers the flow of gas from the pressure generator to a patient. A valve assembly communicates gas from the second conduit to the first conduit to control the pressure or a rate of the flow of gas in the second conduit. By communicating gas from the second conduit to the first conduit, the noise associated with exhausting gas from the second conduit is muffled by the tortuous path of the first conduit.

17 Claims, 8 Drawing Sheets

U.S. PATENT DOCUMENTS

| | | | |
|---|---|---|---|
| 5,241,955 A | 9/1993 | Dearman et al. | |
| 5,271,389 A | 12/1993 | Isaza et al. | |
| 5,551,419 A | 9/1996 | Froehlich et al. | |
| 5,577,496 A | 11/1996 | Blackwood et al. | |
| 5,598,838 A | 2/1997 | Servidio et al. | |
| 5,630,411 A * | 5/1997 | Holscher | 128/205.24 |
| 5,632,298 A * | 5/1997 | Artinian | 137/102 |
| 5,694,923 A | 12/1997 | Hete et al. | |
| 5,694,926 A * | 12/1997 | DeVries et al. | 128/205.24 |
| 5,704,346 A | 1/1998 | Inoue | |
| 5,841,080 A | 11/1998 | Iida et al. | |
| 5,868,133 A * | 2/1999 | DeVries et al. | 128/204.21 |
| 5,881,722 A * | 3/1999 | DeVries et al. | 128/204.21 |
| 5,927,275 A * | 7/1999 | Loser et al. | 128/205.24 |
| 5,931,159 A | 8/1999 | Suzuki et al. | |
| 5,953,713 A | 9/1999 | Behbehani et al. | |
| 5,960,831 A * | 10/1999 | Borcea et al. | 137/625.65 |
| 6,023,830 A | 2/2000 | Cole et al. | |
| 6,041,780 A | 3/2000 | Richard et al. | |
| 6,050,260 A | 4/2000 | Daniell et al. | |
| 6,148,816 A * | 11/2000 | Heinonen et al. | 128/205.24 |
| 6,152,135 A | 11/2000 | DeVries et al. | |
| 6,279,574 B1 * | 8/2001 | Richardson et al. | 128/204.18 |
| 6,615,831 B1 * | 9/2003 | Tuitt et al. | 128/204.18 |

* cited by examiner

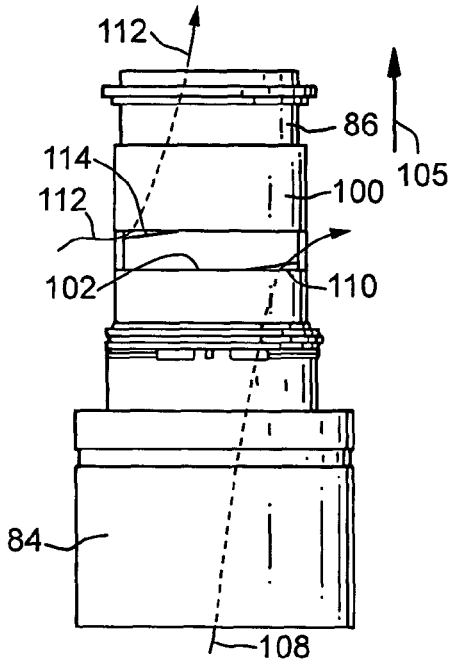
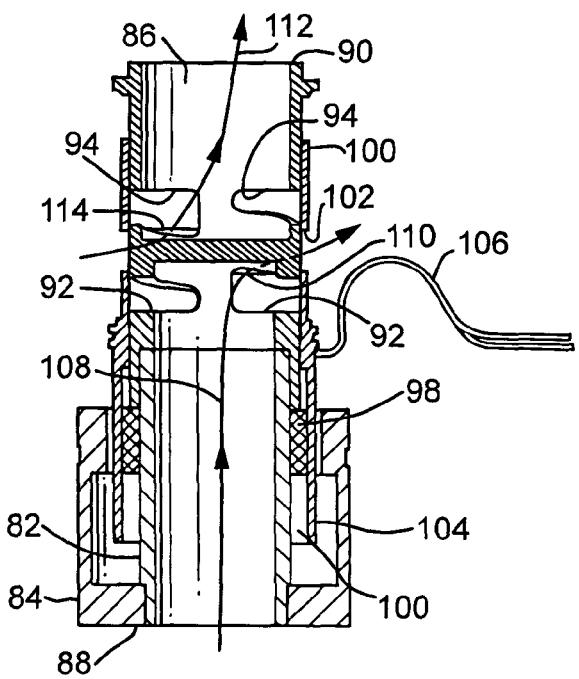
FIG. 6A  FIG. 6B
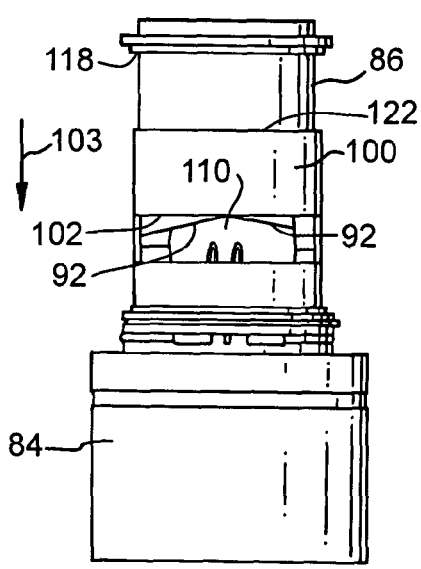
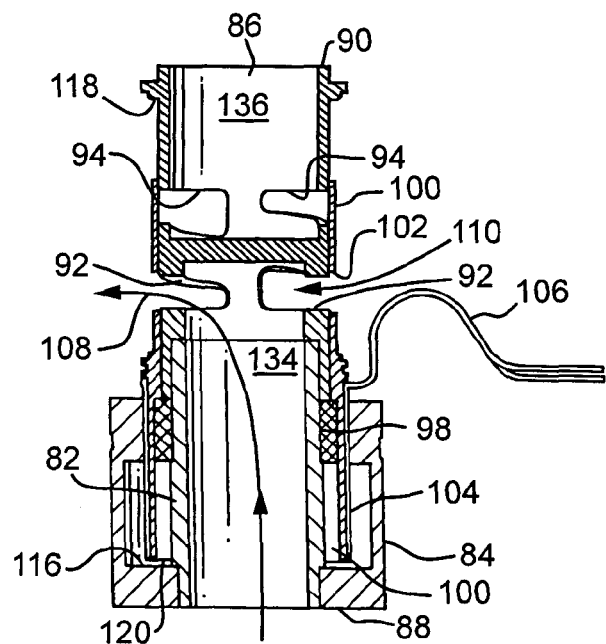
FIG 7A  FIG 7B

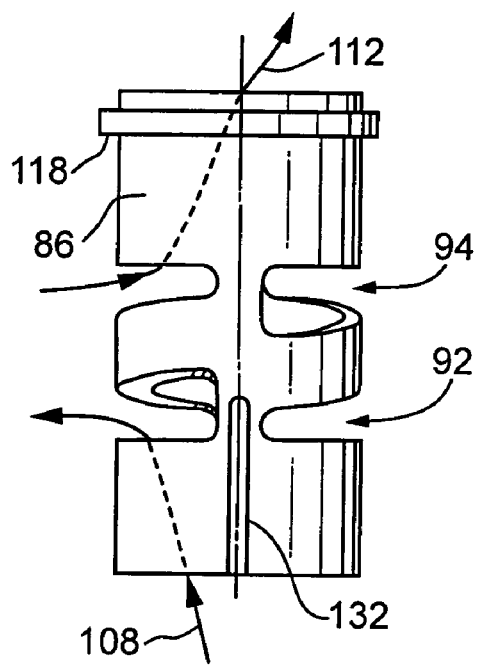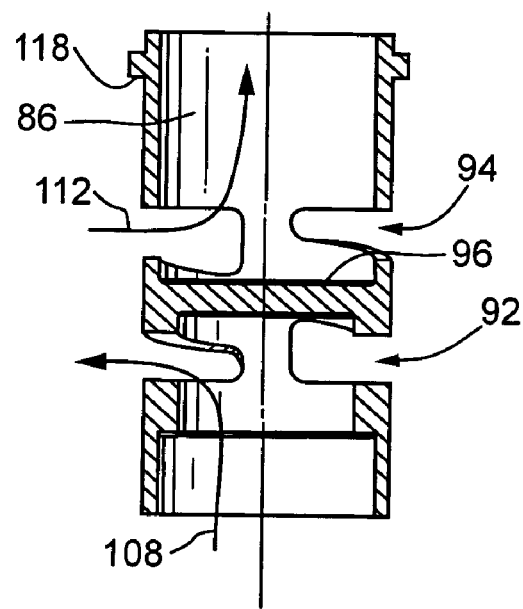
*FIG. 8A*   *FIG. 8B*
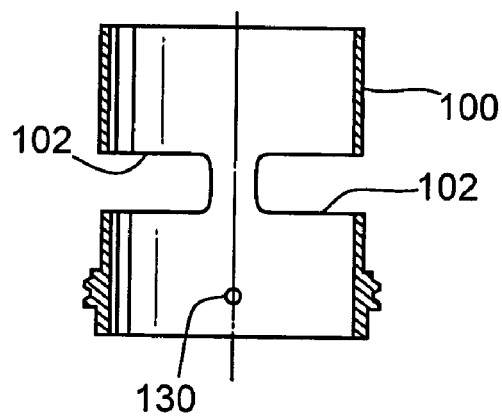
*FIG 9*

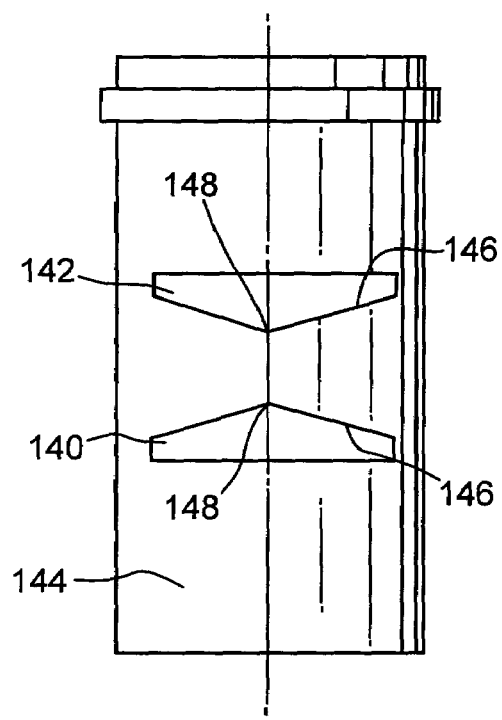 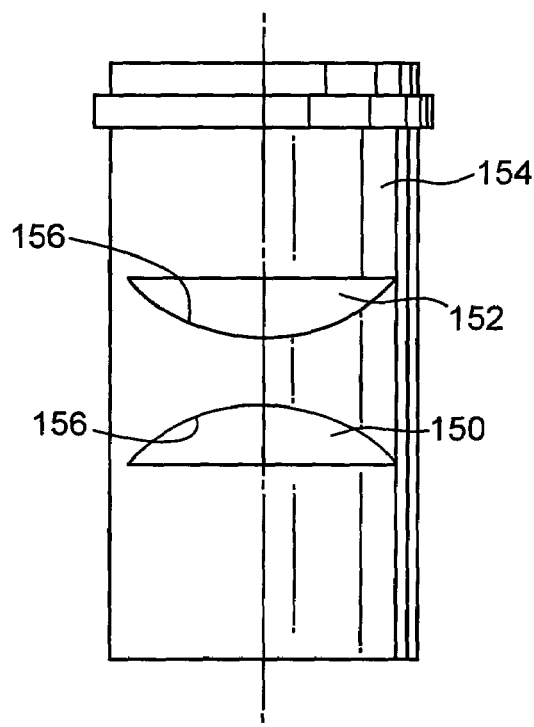
FIG. 10  FIG. 11

PRESSURE SUPPORT SYSTEM AND METHOD AND A PRESSURE CONTROL VALVE FOR USE IN SUCH A SYSTEM AND METHOD

CROSS-REFERENCE TO RELATED APPLICATIONS

This in a Continuation under 35. U.S.C. § 120 of U.S. patent application Ser. No. 09/347,071 filed Jul. 2, 1999 now U.S. Pat. No. 6,615,831.

BACKGROUND OF THE INVENTION

1. Field of the Invention

The present invention pertains to a pressure support system and a method of providing pressure support to a patient, and, more particularly, to a pressure support system and method having enhanced noise reduction, as well as a pressure control valve assembly for use in a pressure support system.

2. Description of the Related Art

Pressure support systems that provide a flow of gas to an airway of a patient at an elevated pressure via a patient circuit to treat a medical disorder are well known. For example, it is known to use a continuous positive airway pressure (CPAP) device to supply a constant positive pressure to the airway of a patient to treat obstructive sleep apnea (OSA). It is also known to provide a positive pressure therapy in which the pressure of gas delivered to the patient varies with the patient's breathing cycle or varies with the patient's effort to increase the comfort to the patient. It is further known to provide a positive pressure therapy in which the pressure provided to the patient changes based on the detected conditions of the patient, such as whether the patient is snoring or experiencing an apnea, hypopnea or upper airway resistance.

Conventional pressure support devices typically include a pressure generator, for example, a blower, piston, or bellows, that creates a flow of breathing gas at a pressure greater than the ambient atmospheric pressure. A patient circuit delivers the elevated pressure breathing gas to the airway of the patient. Typically, the patient circuit includes a conduit, e.g., a single limb or lumen, having one end coupled to the pressure generator and a patient interface device coupled to the other end of the conduit. The patient interface connects the conduit with the airway of the patient so that the elevated pressure gas flow is delivered to the patient's airway. Examples of patient interface devices include a nasal mask, nasal and oral mask, full face mask, nasal cannula, oral mouthpiece, tracheal tube, endotracheal tube, or hood. A single limb patient circuit includes an exhalation port, also referred to as an exhalation vent, exhaust port, or exhaust vent, to allow expired gas from the patient to exhaust to atmosphere. Generally, the exhaust vent is located in the conduit near the patient interface or in the patient interface device itself.

Many of these pressure support devices are used at night, especially where the function of the pressure support system is to treat a breathing disorder that occurs during sleep, such a sleep apnea. For this reason, the pressure support system must be quiet so as not to arouse the user or the user's bed partner. One source of noise addressed by the present invention is the exhaust assembly downstream of the pressure generator, which exhausts gas from the patient circuit to atmosphere. This is typically done in order to maintain the correct pressure or flow in the patient circuit. Typically, this exhaust assembly and associated exhaust path are located within a housing that contains the pressure generator.

Conventional pressure support devices with this configuration attempt to minimize noise due to exhausting of gas through the pressure control valve assembly to atmosphere by providing a dedicated muffler in the exhaust path. However, such a muffler is disadvantageous in that it adds significant cost, size, and weight to the pressure support system.

An example of a conventional pressure support system 1 with this configuration is shown in FIG. 1. The conventional system includes a blower assembly 2 having a blower housing 3, a fan 4 contained within the blower housing, a motor 5 for driving fan 4, an inlet or intake 6, and an outlet 8. These features are collectively referred to as a pressure generator 7. Inlet 6 is coupled to a first conduit 10 that communicates the inlet of the blower assembly to atmosphere. Outlet 8 of blower assembly 2 is coupled to a second conduit 12 that communicates a flow of breathing gas having an elevated pressure relative to ambient atmosphere created by the blower assembly to a third conduit 13 for delivery to a patient 20. A single housing 15, generally identified by the dashed line in FIG. 1, houses the components of the pressure support system.

Third conduit 13 has a first end 14 coupled to an end of second conduit 12 opposite outlet 8. Third conduit 13 also has a second end 16, opposite first end 14, that is coupled to a patient interface 18, which can be secured to patient 20 in a manner known in the art. Third conduit 13 is typically a flexible conduit to allow the patient to move freely while using the pressure support system. All of the conduits and devices for delivering the flow of breathing gas from the blower assembly to the patient's airway define a patient circuit 19. In the embodiment illustrated in FIG. 1, patient circuit 19 includes second conduit 12, third conduit 13, and patient interface 18.

During operation, motor 5 drives fan 4, thereby creating, at intake 6, a negative pressure relative to the pressure of the fluid, e.g., air, in the ambient atmosphere. In response to this negative pressure, fluid in the ambient atmosphere is drawn through first conduit 10 and intake 6 into blower housing 3, wherein the operation of fan 4 increases the pressure of the fluid. The fluid pressurized by fan 4 is delivered from blower housing 3 at outlet 8 into second conduit 12. The pressurized fluid flows through third conduit 13 to patient interface 18 for receipt by patient 20. An exhaust port 22 is provided at second end 16 of third conduit 13 for exhausting gases, such as the exhaled gases from the patient, to ambient atmosphere. Exhaust port 22 can have a variety of configurations that are well known in the art, and can be provided in third conduit 13, as shown, or in patient interface 18.

As noted above, there are many instances where it is desirable to control the pressure, and, hence, the flow of fluid, delivered to the patient by the pressure support system. For example, it is known to provide a continuous positive airway pressure "CPAP" device with the ability to change the pressure or flow of fluid delivered to the patient so that a commonly designed device can be used to provide pressure support therapy to patients with different pressure support prescription levels. Typically, the patient's therapy pressure is determined in a sleep study and then the CPAP device prescribed and is set to output that prescription pressure at all time during its operation. An example of a CPAP device that operates in this manner is the REMstar® and Solo® family of devices manufactured and distributed by Respironics, Inc. of Pittsburgh, Pa.

Unlike a CPAP device, which outputs a constant pressure at all times during its operation, it is also known, as described above, to provide a pressure support therapy in which the pressure of breathing gas delivered to the patient varies during the course of treatment. For example, it is known to vary the pressure of breathing gas delivered to the patient in synchronization with the patient's breathing cycle so that a lower pressure is delivered to the patient during the expiratory phase of the breathing cycle than is delivered during the inspiratory phase, so that the patient is not breathing out against a relatively high pressure. This mode of pressure support is typically referred to as "bi-level" pressure support. Examples of pressure support devices that have the ability to operate in this bi-level mode of ventilation are the BiPAP® family of devices manufactured and distributed by Respironics, Inc.

It is also known to vary the pressure of breathing gas provided to the patient based on the detected conditions of the patient, such as whether the patient is snoring or experiencing an apnea, hypopnea, or upper airway resistance. This mode of pressure support is typically referred to as "auto" or "smart" pressure support because the pressure support device determines the optimum pressure to deliver to the patient. An example of a device that adjusts the pressure delivered to the patient based on the whether or not the patient is snoring is the Virtuoso® CPAP family of devices manufactured and distributed by Respironics, Inc. An example of a pressure support device that actively tests the patient's airway to determine whether obstruction, complete or partial, could occur and adjusts the pressure output to avoid this result is the Tranquility® Auto CPAP device also manufactured and distributed by Respironics, Inc.

Typically, these latter two conventional modes of pressure support, i.e., bi-level and "auto" or "smart" CPAP modes of pressure support, require some means for the pressure support system to detect the condition of the patient so that the pressure or flow provided to the patient can be controlled based on this condition. For example, a bi-level pressure support device typically includes a flow sensor 24 that detects the flow of fluid in patient circuit 19 and a pressure sensor 26 that detects the pressure at patient interface 18. A controller 28 receives the flow signal and the pressure signal from flow sensor 24 and pressure sensor 26, respectively, and uses this information to determine when the patient has transitioned from the inspiratory phase to the expiratory phase of the breathing cycle, or vice versa, to control the pressure accordingly. In the "auto" or "smart" CPAP mode of pressure support, these pressure and flow sensors, or other sensors, such as a microphone, are used to detect snoring, apneas, hypopneas, etc. In addition, it is known to have the less sophisticated CPAP devices monitor the pressure or flow of breathing gas delivered to the patient and adjust the pressure or flow in a feedback fashion to meet the desired prescription pressure level.

There are several techniques for controlling the pressure or flow of breathing gas to the patient in a pressure support device. As discussed above, one such method involves providing a pressure control valve assembly 30 in patient circuit 19 to exhaust a portion of the breathing gas in patient circuit 19 to atmosphere through an exhaust conduit 32, thereby decreasing the pressure and flow delivered to the patient. Controller 28 typically controls the operation of valve assembly 30 based on the detected conditions of the patient to control the pressure or flow of breathing gas provided to the patient. Due to the relatively large amount of noise associated with this exhaust flow, which is indicated by arrow 34 in FIG. 1, it is known to provide a muffler 36 in exhaust conduit 32. However, as noted above, the present inventors appreciated that such a muffler is undesirable in that it adds significant cost, size, and weight to the pressure support system.

As noted above, the pressure control technique shown in FIG. 1 uses a pressure control valve assembly 30 to selectively exhaust gas from the patient circuit to control the pressure of the gas in the circuit during the patient breathing cycle. One conventional pressure control valve assembly 30' that accomplishes this function is taught in U.S. Pat. No. 5,694,923 to Hete et al. and is shown in FIG. 2. Pressure control valve assembly 30' taught by Hete et al. uses two poppet type valves 40 and 42. Valve 40 controls exhaust of gas from patient circuit 19 to atmosphere and valve 42 restricts the flow of gas through patient circuit 19 provided by a pressure generator (not shown). This combination of valves is controlled by a controller 44 and actuators 46 to control the pressure or flow of fluid through the patient circuit delivered to the patient.

For example, when operating in the bi-level mode of ventilation, the inspiratory positive airway pressure (IPAP) is set by controlling one of more of the following: (1) the amount of flow restriction provided by valve 42, (2) the amount of exhaust to atmosphere provided by valve 40, and (3) the amount of flow provided by the pressure generator. During exhalation, the expiratory positive airway pressure (EPAP) is set by closing valve 42, either completely or partially, and operating valve 40 to control the amount of exhaust from patient circuit 19 to atmosphere. By completely blocking the flow from the pressure generator using valve 42 or by making sure the flow out of valve 40 is greater than the flow through valve 42, the patient does not exhale against any pressure provided by the pressure generator. The EPAP pressure in patient circuit 19 created by the patient's exhalation is regulated by controlling the amount of exhaust provided by valve 40.

This pressure control technique is advantageous in that it allows for a rapid transition between inspiration and expiration pressures so that the patient does not exhale against a pressure or flow provided by the pressure generator and immediately receives the IPAP pressure at the start of inspiration. In addition, the two valves can be controlled in tandem to minimize the amount of gas vented to atmosphere while still providing the proper pressure IPAP and EPAP levels. However, this pressure control technique is disadvantageous in that it requires two valve elements, which increases the cost and size of the pressure support system.

Another conventional pressure control valve assembly 30" that exhausts gas to atmosphere, at least during a portion of the breathing cycle, to control the pressure in the patient circuit is taught in U.S. Pat. No. 5,598,838 to Servidio et al. and is shown in FIGS. 3A and 3B. Pressure control valve assembly 30" taught by Servidio et al. uses a slideable hollow piston 50 that moves as shown in FIGS. 3A and 3B to control the pressure in patient circuit 19. An actuator 52 provides the necessary force to move piston 50. In a first position shown in FIG. 3A, piston 50 allows gas to flow from the pressure generator to the patient while blocking flow out of patient circuit 19 through exhaust ports 54. The IPAP level in patient circuit 19 is set by controlling one of more of the following: (1) the amount of flow restriction provided by piston 50 over inlet port 56 and (2) the amount of flow provided by the pressure generator. In a second position shown in FIG. 3B, piston 50 blocks the flow of gas from the pressure generator while exhausting gas from patient circuit 19 through exhaust ports 54. The EPAP level is set by controlling the amount of exhaust from patient circuit 19 to atmosphere through exhaust port 54, which is accomplished by controlling the position of piston 50.

Pressure control valve assembly 30″ is advantageous in that it uses a single valve element, namely piston 50, to control the IPAP and EPAP pressures in patient circuit 19. This configuration is also advantageous in that it can be used to measure the pressure in patient circuit 19 by determining the force that urges piston to move toward the position shown in FIG. 3B. This piston pressure control valve, however, requires moving a relatively large piston in order to control the pressure in the patient circuit. In addition, during expiration, actuator 52 must urge piston 50 to the right to balance against the pressure in patient circuit 19 that tend to urge the piston to the left. For these reasons, actuator 52 must be able to deliver a relatively large force to control the position of piston 50. In addition, because the pressure in the patient circuit affects the position of the piston, it is relatively difficult to control the position of the piston, and, hence the pressure in the patient circuit, with a high degree of accurately with a minimal amount of energy. This valve assembly also does not allow for gas to be delivered from the pressure generator into the patient circuit while simultaneously exhausting gas from the patient circuit, which is helpful to ensure that the pressure generator and the gas in the pressure generator does not become over heated by the continued operation of the pressure generator while the flow from the pressure generator is blocked.

The two above-described pressure control techniques involve restricting the flow of gas from the pressure generator into the patient circuit or exhausting gas from the patient circuit, or both in the case of the dual poppet valve system, to control the pressure or flow of breathing gas delivered to the patient. However, another technique exists for controlling the pressure or flow of breathing gas delivered to the patient. This third technique involves controlling only the motor speed of the pressure generator, such as the motor speed of a blower that is used to create a flow of gas, so that the pressure generator outputs the gas at the desired rate or pressure without additional pressure control valves.

A disadvantage with a pressure support system that uses motor speed to control the pressure or flow of the gas delivered to the patient is that it is difficult to rapidly transition from one pressure level to another. For example, during a bi-level mode of ventilation it is necessary to provide breathing gas to a patient at a relatively high level during the inspiratory phase of their breathing cycle and to provide the breathing gas at a relatively low level during the expiratory phase. This can require changing the pressure level of the breathing gas delivered to the patient a relatively large amount, such as 15 cm $H_2O$, over a relatively short period of time, such as 0.5 seconds. Because of the relatively high rotational velocity or the relatively large mass of the blower, i.e., impeller, it is difficult to increase or decrease the motor speed by the required amount in the necessary short time period to achieve these pressure variations.

If the blower speed is not reduced fast enough during the transition from the inspiratory to the expiratory phase of the breathing cycle, for example, the patient begins exhaling against a pressure head, which is generally not conducive to patient comport. Changing the motor speed to control the pressure or flow delivered to the patient also subjects the pressure generator, specifically the blower, to relatively large mechanical and electrical stresses, which increase the wear on the blower. Increased wear may reduce the blower's operating life or require that the blower be manufactured to withstand such stresses, which increases the overall cost of the blower.

SUMMARY OF THE INVENTION

It is, therefore, an object of the present invention to provide a pressure support system that overcomes the disadvantages associated with conventional pressure support systems. In particular, it is an object of the present invention to provide a pressure support system with enhanced noise reduction. This object is achieved according to one embodiment of the present invention by providing a pressure support system that includes a pressure generator having an inlet portion and an outlet portion for generating a flow of gas. The pressure support system also includes a first conduit having a first end open to ambient atmosphere and a second end coupled to the inlet portion of the pressure generator to supply gas from a gas source, such as ambient atmosphere, to the pressure generator. The first conduit defines a tortuous path between the first end and the second end. A second conduit coupled to the outlet portion of the pressure generator delivers the flow of gas from the pressure generator to a patient. A valve assembly is connected to the first conduit and the second conduit to communicate gas from the second conduit to the first conduit to control the pressure or rate of flow of gas in the second conduit. By communicating gas from the second conduit to the first conduit, the noise associated with exhausting gas from the second conduit is muffled by the tortuous path of the first conduit.

It is yet another object of the present invention to provide a method of providing pressure support that does not suffer from the disadvantages associated with conventional pressure support techniques and that has enhanced noise reduction. This object is achieved by providing a method that includes (1) communicating an inlet of a pressure generator to a source of gas via a first conduit, (2) generating a flow of gas with the pressure generator, (3) communicating the flow of gas from the pressure generator to a patient via a second conduit, and (4) communicating gas from the second conduit to the first conduit to control the pressure or rate of flow of gas in the second conduit. As noted above, by communicating gas from the second conduit to the first conduit, the noise associated with exhausting gas from the second conduit is muffled by the tortuous path of the first conduit.

It is a further object of the present invention to provide a pressure control valve and a pressure support system having a pressure control valve that overcomes the disadvantages associated with conventional pressure control techniques. This object is achieved by providing a valve assembly suitable for use in a pressure support system, wherein the valve assembly includes a hollow first cylinder having an open first end, an open second end, a blower discharge slot defined in a wall thereof, an exhaust intake slot defined in the wall thereof between the blower discharge slot and the second end, and a separating plate disposed in the first cylinder between the blower discharge slot and the exhaust intake slot. The valve assembly also includes a hollow second cylinder having a first slot defined in a wall thereof. The second cylinder is positioned coaxially around the first cylinder. An actuator moves the second cylinder axially with respect to the first cylinder to control the amount of overlap between the first slot and the blower discharge slot and amount of overlap between the first slot and the exhaust discharge slot.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 6A and 6B are side and sectional views, respectively, of the pressure control valve assembly of FIG. 5 showing the outer cylinder in a first position relative to the inner cylinder;

FIGS. 7A and 7B are side and sectional views, respectively, of the pressure control valve assembly of FIG. 5 showing the outer cylinder in a second position relative to the inner cylinder;

FIGS. 8A and 8B are side and sectional view, respectively, of an inner cylinder in the pressure control valve assembly of FIG. 5;

FIG. 9 is a side sectional view of a portion of an outer cylinder in the pressure control valve assembly of FIG. 5; and FIGS. 10 and 11 illustrate alternative embodiments of the slots provided in the inner cylinder of the pressure control valve assembly.

DETAILED DESCRIPTION OF THE PRESENTLY PREFERRED EXEMPLARY EMBODIMENTS

Figure 1:
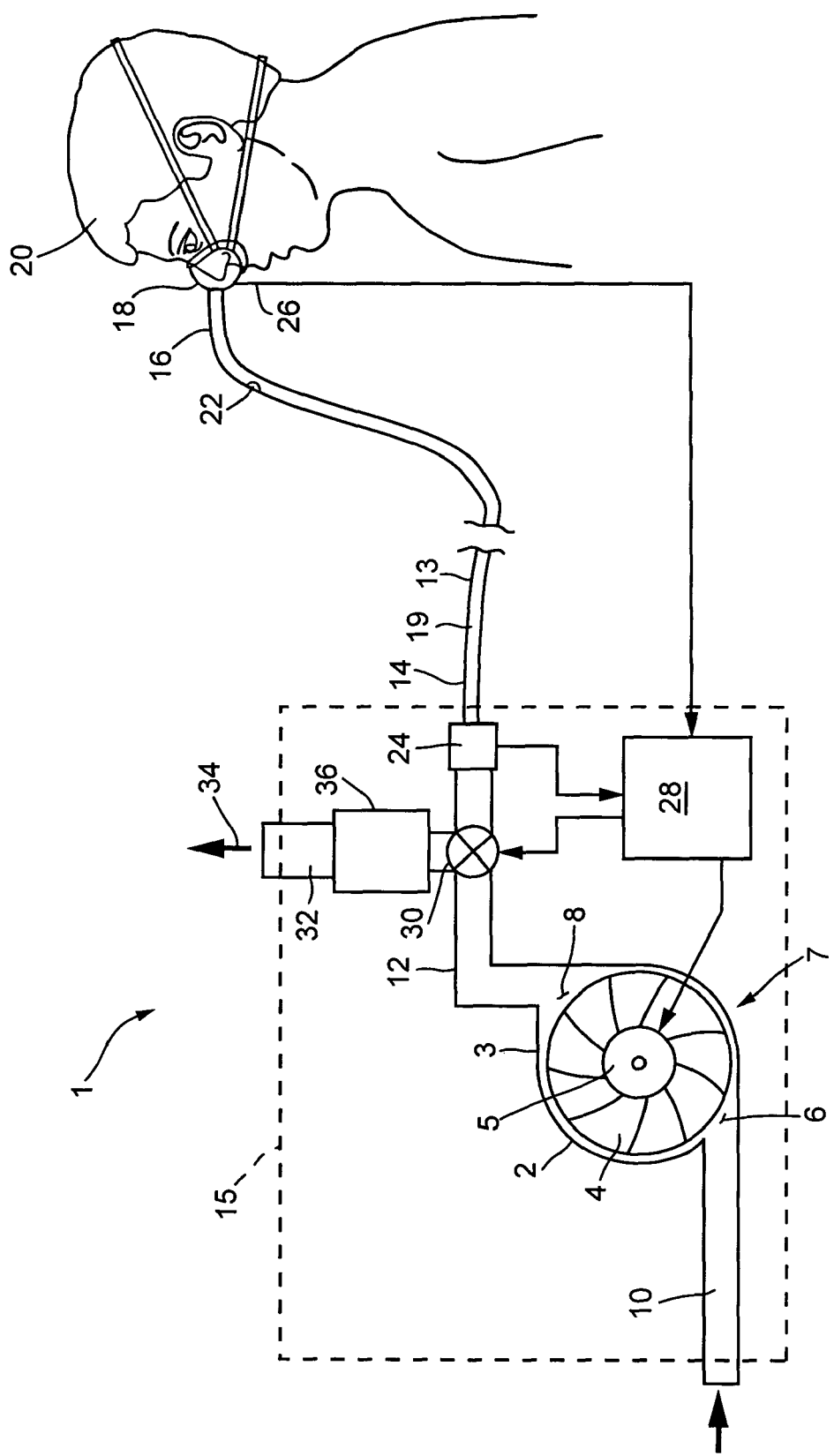
FIG. 1 is a schematic view of a conventional pressure support system.
Figure 2:
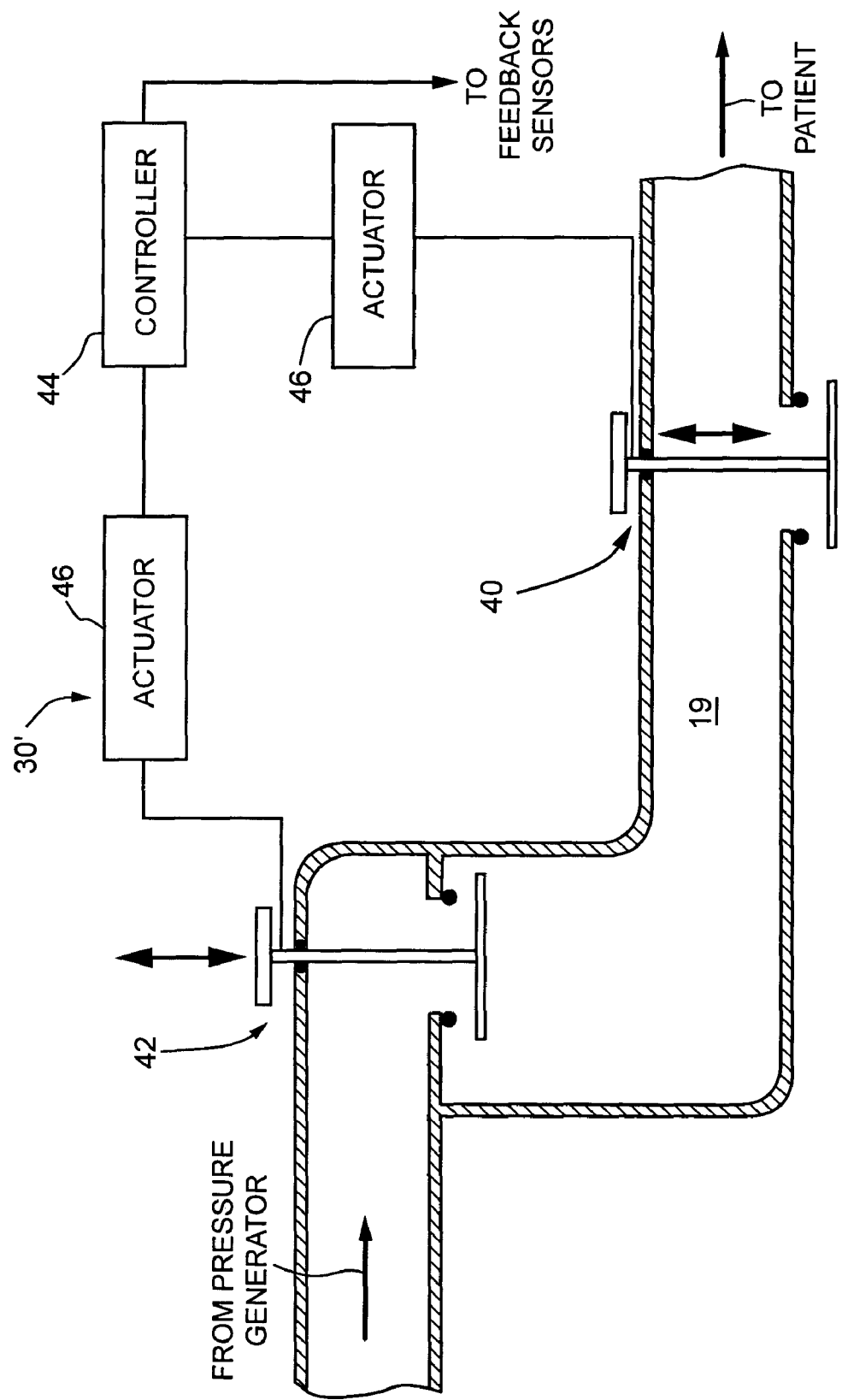
FIG. 2 is a schematic view of a conventional pressure control valve assembly.
Figure 3A:
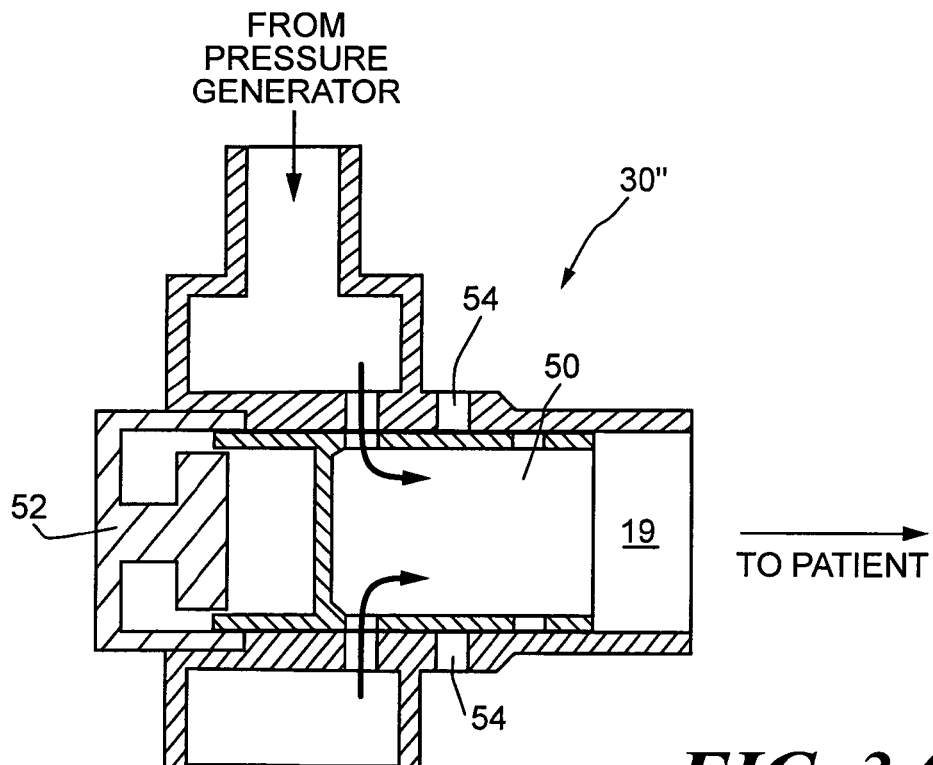
FIGS. 3A and 3B are sectional views of another conventional pressure control valve assembly.
Figure 3B:
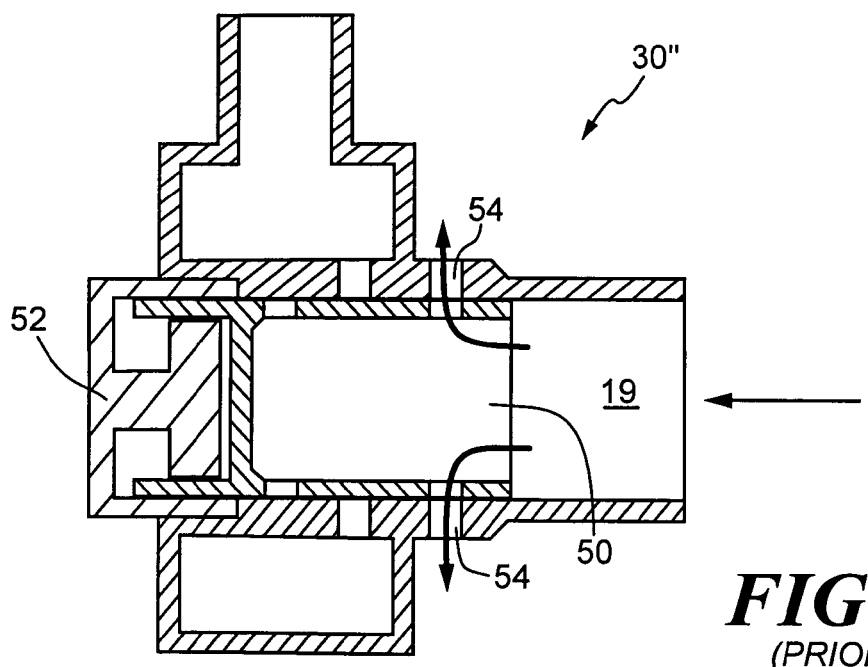
Figure 4:
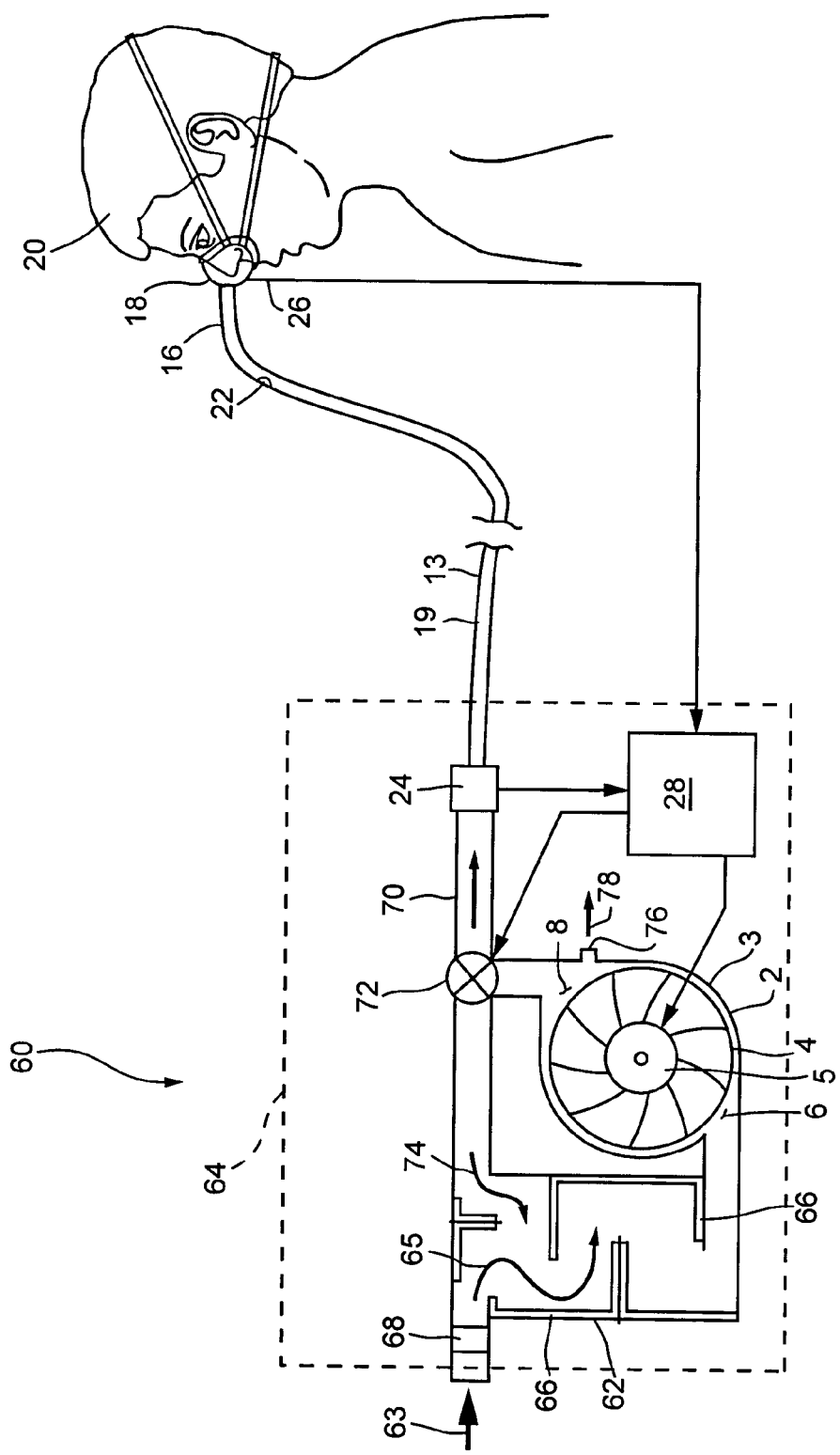
FIG. 4 is a schematic view of a pressure support system in accordance with the principles of the present invention.

A pressure support system according to the principles of the present invention will now be described with reference to FIG. 4. For simplicity of description, like elements in the description of the present invention shown in FIG. 4 and in the description of the conventional pressure support systems shown in FIG. 1 have like reference numbers.

Pressure support system 60 includes a pressure generator in the form of a blower assembly 2 having a blower housing 3, a fan 4 contained within the blower housing, a motor 5 for driving fan 4, an inlet potion or intake 6, and an outlet portion 8. Inlet 6 is coupled to a first conduit 62 that communicates the inlet of the blower assembly to a source of gas 63 for the pressure generator, such as ambient atmosphere. It is to be understood that other sources of gas can be used instead of, or in addition to, the air from the ambient atmosphere. For example, a supply of oxygen or an oxygen mixture can be provided as source of breathing gas. A housing 64 identified by the dashed line in FIG. 4 contains these elements of the pressure support system.

First conduit 62 defines a tortuous path, generally indicated by arrow 65 from its inlet to atmosphere to inlet 6 of blower assembly 2. Preferably, a noise dampening material 66, such as foam, is provided on the walls of the first conduit to absorb noise. In the illustrated exemplary embodiment, a filter 68 is provided at the inlet of the first conduit to prevent particulate matter from entering the blower assembly. Filter 68 also provides a sound dampening function so that the combination of the tortuous, baffled path defined by the first conduit and the sound dampening filter effectively function as a muffler for the pressure support system.

An outlet 8 of blower assembly 2 is coupled to a second conduit 70 that communicates a flow of gas generated by the blower assembly a third conduit 13 for delivery to a patient 20. A valve 72 is provided in second conduit 70 for controlling the rate or pressure of the flow of fluid delivered to the patient. In an exemplary embodiment of the present invention, valve 72 controls the rate or pressure of the flow of gas in the second conduit by exhausting gas from the second conduit. It is to be understood, however, that another embodiment of the present invention contemplates that valve 72 controls the rate or pressure of the flow of gas in the second conduit by restricting the flow from blower assembly 2 in addition to exhausting gas from the second conduit. The present invention also contemplates changing the speed of motor 5 to control the pressure or rate of flow of gas generated by the blower assembly.

Instead of exhausting gas from the second conduit into atmosphere, as done in conventional pressure support system, valve 72 is coupled to first conduit 62 so that the exhaust gas from second conduit 70 is delivered to first conduit 62, as indicated by arrow 74. By communicating gas from second conduit 70 to the first conduit 62, the noise associated with exhausting gas from the second conduit 70 is muffled by the elements of the first conduit, such as tortuous path of the first conduit, noise dampening materials 66, and filter 68. In this way, the first conduit effectively functions as a muffler for the exhaust of gas from the second conduit.

Pressure support system 60 includes a port 76 defined in second conduit 70 downstream of the blower assembly for directing a bleed off flow of gas from the second conduit, as indicated by arrow 78. Preferably, port 76 is sized such that amount of bleed off flow therefrom is relatively small, such as 10 liters per minute when the pressure generator outputs a pressure of 40 cmH$_2$O. Of course the flow rate from this fixed diameter orifice will vary as the pressure output by the pressure generator varies. This bleed off flow of gas has two functions. It allows gas to be drawn from the blower assembly regardless of the operation of valve 72 or the flow in conduit 70. For example, if valve 72 completely obstructs the flow from the blower so that no gas flows into patient circuit 19, drawing gas from the blower ensures that the blower assembly and the gas in the blower does not become over heated, which can occur if the blower continues to operate without venting gas from the blower. Bleed off flow of gas 78 provided by port 76 also serves to cool the components of the pressure support system, such as the electronic circuitry associated with controller 28 and motor 5.

Pressure support system 60 can be operated as a CPAP device, a bi-level device, or as an "auto" or "smart" CPAP device based on how pressure controller 28 controls the operation of motor 5 and valve 72. For example, in a bi-level mode of operation, controller 28 receives flow signals and pressure signals from flow sensor 24 and pressure sensor 26, respectively, to distinguish between the inspiratory and expiratory phase of the patient's breathing cycle as is known in the art. Controller 28 sets the IPAP and EPAP levels by controlling one or more of the following: (1) the degree of restriction to flow from second conduit 70 to first conduit 62, (2) the degree of restriction to flow from the pressure generator to patient circuit 19, and (3) the speed of motor 5.

For example, during the expiratory phase, controller 28 transitions from the IPAP level to the EPAP level by increasing the amount of flow of gas exhausted from second conduit 70 to first conduit 62 by valve 72. The end of first conduit 62 near inlet 6 is at a negative pressure while the blower is operating. If the second conduit is connected to the first conduit near inlet 6, communicating the second conduit with the first conduit allows for a relatively rapid decrease in pressure within the second conduit and, hence, within the patient circuit.

It should be noted that when a patient breathes into patient interface device 18 and conduit 13, most of the patient's exhalation is exhausted to atmosphere through exhaust port 22. While some of the patient's exhalation may move up patient circuit 19 toward valve 72, it is highly unlikely that any of the patient exhalation will reach valve 72 so that it is diverted into the inlet of blower assembly 2 via the coupling between second conduit 70 and first conduit 62. It should be further noted that the second conduit can be coupled to first conduit 62 at a variety of locations. However, it is preferable to couple the second conduit to the first conduit at a location along the first conduit sufficiently far from the inlet of the first conduit to take advantage of the sound dampening provided by the tortuous path of the first conduit.

An exemplary embodiment of valve 72 according to the principles of the present invention will now be discussed below with reference to FIGS. 5–9 and with continuing reference to FIG. 4. Valve 72, which is also referred to as a valve assembly due to the fact that the valve is defined by a number of parts, includes a hollow, first or inner cylinder 80, which includes a center barrel 82, a first barrel 84 and a second barrel 86. First barrel 84 and second barrel 86 are positioned at opposite ends of center barrel 82 and coaxially therewith. Inner cylinder 80 has an open first end 88, an open second end 90, a blower discharge slot 92 defined in a wall of second barrel 86 and an exhaust intake slot 94 defined in the wall of second barrel 86 between blower discharge slot 92 and second end 90. A separating plate 96 (shown in phantom in FIG. 5) is positioned in inner cylinder 80 and, more particularly, in second barrel 86, between blower discharge slot 92 and exhaust intake slot 94 for obstructing or preventing the flow of gas therebetween.

An annular permanent magnet 98 is secured around an end of center barrel 82 opposite first barrel 84. Preferably, magnet 98 is glued to the exterior of center barrel 82, with slots 99 being provided in the center barrel to facilitate the attachment of these two members. It is to be understood that other techniques for attaching the magnet to the center barrel are contemplated by the present invention. For example, magnet 98 can be threaded onto corresponding threads in the exterior surface of center barrel 82 or press fit onto the center barrel.

Valve assembly 72 also includes a second or outer cylinder 100 configured to be received around magnet 98 and inner cylinder 80 and to move axially between first end 88 and second end 90 of inner cylinder 80. Outer cylinder 100 includes a first slot 102 defined in the wall thereof. In an assembled configuration, first slot 102 is capable of overlapping blower discharge slot 92 and exhaust intake slot 94 individually or simultaneously.

Figure 5:
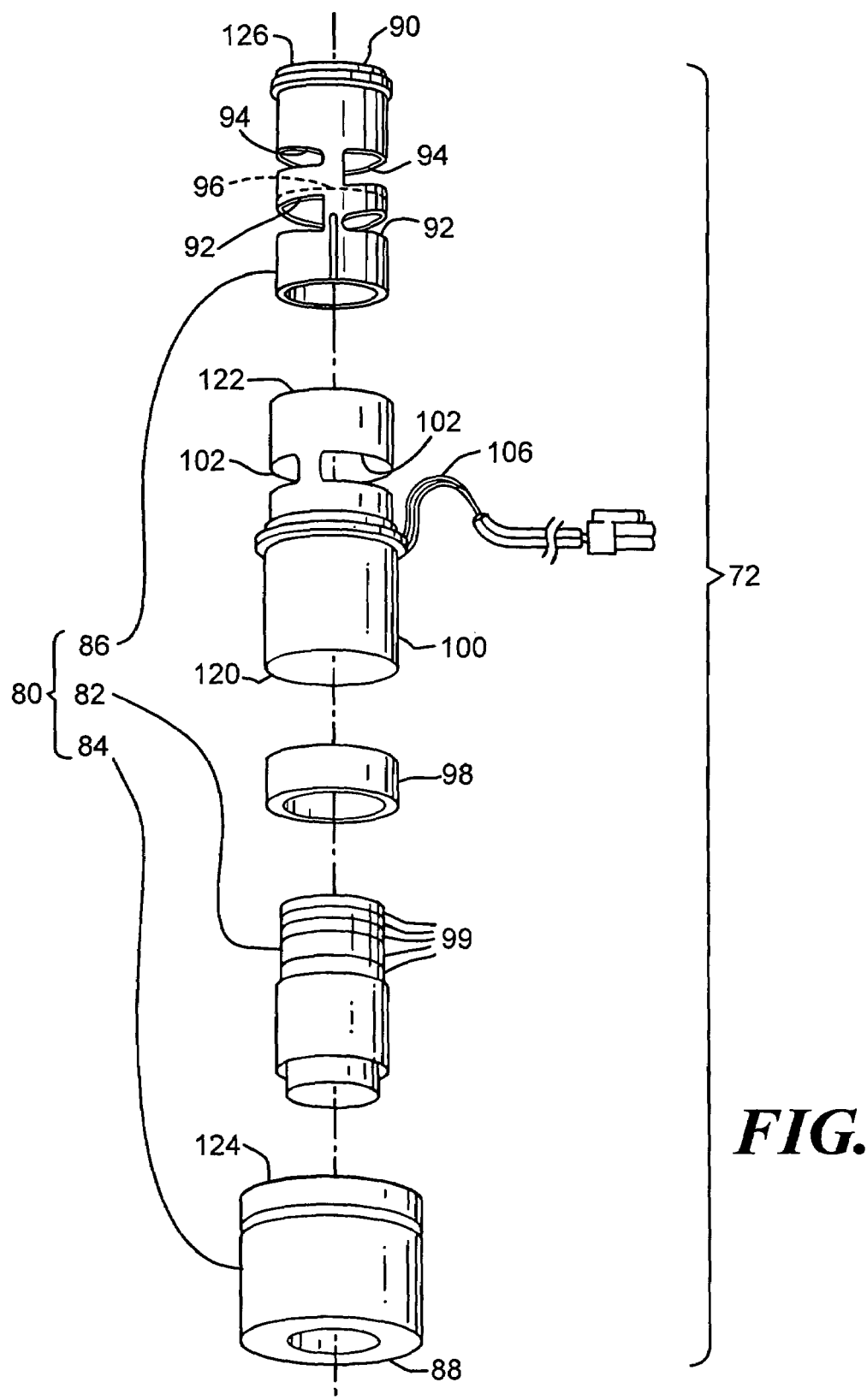
FIG. 5 is an exploded perspective view of a pressure control valve assembly for use in a pressure support system, including the pressure support system of FIG. 4.

A coil 104 is secured around outer cylinder 100 in magnetic flux coupled relation with magnet 98. It should be noted that FIG. 5 illustrates a portion or outer cylinder 100 without the coil. The present invention contemplates that coil 104 can be attached to the end of the portion of the outer cylinder or can be wound around the outer cylinder as shown in FIGS. 6B and 7B. As shown in FIGS. 5, 6B, and 7B, a wire 106 extends from coil 104 for passing a current through the coil. Coil 104 is configured to receive DC current from controller 28. According to one embodiment of the present invention, in response to receiving DC current of a first polarity, coil 104 urges outer cylinder 100 axially relative to inner cylinder 80 in a first direction indicated by arrow 103 in FIG. 7A. When displaced to the maximum amount possible in the first direction, first slot 102 in outer cylinder 100 and blower discharge slot 92 in inner cylinder 80 are aligned and outer cylinder 100 obstructs exhaust intake slot 94 of inner cylinder 80. FIGS. 7A and 7B illustrate outer cylinder 100 displaced as far as possible in the first direction with first slot 102 and blower discharge slots 92 being generally aligned with one another so that a flow of gas, as indicated by arrow 108, flows from the pressure generator out of the aperture 110 defined by the overlap of first slot 102 and blower discharge slots 92. Movement of outer cylinder 100 relative to inner cylinder 80 changes the size of aperture 110 to control a degree of restriction for the flow of gas 108 from the pressure generator into the second conduit, i.e., into patient circuit 19.

Similarly, in response to receiving DC current of a second polarity, opposite the first polarity, coil 104 urges outer cylinder 100 axially relative to inner cylinder 80 in a second direction opposite the first direction as indicated by arrow 105 in FIG. 6A. When displaced to the maximum amount possible in the second direction, first slot 102 of outer cylinder 100 and exhaust intake slot 94 of inner cylinder 80 align and outer cylinder 100 obstructs blower discharge slot 92 of inner cylinder 80. As a result, gas flows, as indicated by arrow 112 into second barrel 86 through an aperture 114 defined by the overlap of first slot 102 and exhaust intake slot 94. This flow of gas can be vented to atmosphere, either directly or through a muffler, or it can be communicated to the intake of the pressure generator, as discussed above with respect to FIG. 4. Movement of outer cylinder 100 relative to inner cylinder 80 changes the size of the aperture 114 to control a degree of restriction for the flow of gas from the second conduit.

While the present invention has been described above as using two polarities of DC current to energize coil 104 to move outer cylinder 100 relative to inner cylinder 80 in one of two longitudinal directions, it is to be understood that other techniques for moving the outer cylinder relative to the inner cylinder are contemplated by the present invention. For example, a spring or other similar mechanism can be used to urge the outer cylinder in a first direction relative to the inner cylinder and a DC current through coil 104 can be used to urge the outer cylinder in an opposing direction. This configuration is advantageous in the only on polarity of current is required. However, it does require a constant current through the coil in order to offset the spring bias force of the outer cylinder is to remain in a fixed position relative to the inner cylinder.

Outer cylinder 100 is also capable of being positioned at any one of a number of axial locations relative to inner cylinder 80 to control the size of apertures 110 and 114, and hence the restriction to flows 108 and 112, respectively. For example, by controlling the polarity of DC current supplied to coil 104, controller 28 can create a first fluid path in which pressurized gas is communicated to the patient circuit for delivery to a patient, and can created a second fluid path in which gas is exhausted from the patient circuit, and, preferably, is drawn to intake 6 of blower assembly 2 by the negative pressure created thereat by fan 4.

The present invention contemplates that both of these paths can be created at the same time as shown, for example, in FIGS. 6A and 6B. That is, the present invention contemplates that first slot 102, blower discharge slot 92, and exhaust intake slot 94 can be sized, configured, and arranged in their respectively cylinders such that both blower discharge slot 92 and exhaust discharge slot 94 overlap first slot 102 provided in outer cylinder 100 at the same time. As a result, apertures 110 and 114 are provided simultaneously in the valve assembly so that both flows 108 and 112 exist. This condition is referred to as "cross-over" and is believed to make it possible to control the pressure or flow in the patient circuit in a very stable manner. It can be appreciated that movement of outer cylinder 100 relative to inner cylinder 80 simultaneously changes the size of aperture 110 and aperture 114 to control a degree of restriction for the flow of gas from the pressure generator into the second conduit and a degree of restriction for the flow of gas from the second conduit, preferably to the first conduit.

Inner cylinder 80 includes at opposite ends thereof stops 116 and 118 that coact with ends of outer cylinder 100 to restrict axial movement of the outer cylinder between first end 88 and second end 90 of inner cylinder 80. Preferably, stop 116 at first end 88 is defined by an inner surface of first barrel 84 adjacent center barrel 82, and stop 118 at second end 90 is a shoulder defined on an end of second barrel 86 opposite center barrel 82. Preferably, when an end 120 of outer cylinder 100 contacts surface 116, first slot 102 of outer cylinder 100 and blower discharge slot 92 of inner cylinder 80 are aligned and outer cylinder 100 obstructs exhaust intake slot 94 of inner cylinder 80. See FIGS. 7A and 7B. Similarly, when an end 122 of outer cylinder 100 contacts shoulder 118, first slot 102 of outer cylinder 100 and exhaust intake slot 94 of inner cylinder 80 are aligned and outer cylinder 100 obstructs blower discharge slot 92 of inner cylinder 80.

The present invention contemplates that blower discharge slot 92, exhaust intake slot 94, first slot 102 or any combination of these slots are shaped to have varying mechanical gains. This is accomplished by shaping the slots such that there is not a constant change in cross sectional area for that slot. For example, as perhaps best shown in FIGS. 8A and 8B, a presently preferred embodiment of the invention has blower discharge slot 92 and exhaust intake slot 94 formed diagonally or spirally in the wall of second barrel 86 of inner cylinder 80 and the first slot 102 is formed as a rectangle. This diagonal or spiral edge of blower discharge slot 92 and exhaust intake slot 94 allows for relatively fine control over the size of apertures 110 and 114 to control the degree of restriction to flows 108 and 112 with a high degree of precision. More specifically, the diagonal or spiral edge of blower discharge slot 92 and exhaust intake slot 94 provides an advantageous mechanical gain when the outer cylinder is in the cross-over position shown in FIGS. 6A and 6B that allows for precise control of the size of apertures 110 and 114 and, hence, precise control over the flow of gas therethrough.

It is to be understood that other configurations for blower discharge slot 92, exhaust intake slot 94, and first slot 102 are contemplated by the present invention. For example, as shown in FIGS. 10 and 11 illustrate alternative embodiments for the blower discharge slot and exhaust intake slot 94 provided in the inner cylinder. In FIG. 10, blower discharge slot 140 and exhaust intake slot 142 defined in inner cylinder 144 have edges 146 formed generally diagonally in the wall of the inner cylinder and meet at an apex 148. In FIG. 11, blower discharge slot 150 and exhaust intake slot 152 defined in inner cylinder 154 have edges 156 that are generally semi-circular or arched. It is to be further understood that the blower discharge slot and the exhaust intake slot need not have the same configuration.

The present invention also contemplates that the end of center barrel 82 opposite the threaded end thereof is press fit into end 124 of first barrel 84. Moreover, second barrel 86 preferably includes a gasket 126 on end 90 thereof opposite center barrel 82 and an end of second barrel 86 opposite shoulder 118 is secured to the end of center barrel 82.

In addition, an alignment pin 130 is provided in the interior surface of outer cylinder 100 and a corresponding alignment slot 132 is provided in the exterior surface of second barrel 86 of inner cylinder 80. Pin 130 slides within slot 132 to maintain the correct rotational orientation of the outer cylinder relative to the inner cylinder. Of course, the present invention contemplates that other mechanisms can be used to ensure alignment of these two cylinders, including reversing the pin and slot so that the pin is provided on the inner cylinder and the slot is provided on the outer cylinder. For example, inner and outer cylinders can be made non-circular, i.e., elliptical, oval, triangular, square, hexagonal, so that the matching shape of the two parts prevents any rotational movement of one part relative to the other.

As noted above, it is preferable that a constant, albeit small, bleed off flow of gas be drawn off of the blower assembly to prevent overheating of the blower assembly as well as the gas in the blower assembly. In the embodiment shown in FIG. 4, this bleed off flow is provided by port 76. However, the present invention also contemplates that this bleed off flow can be provided by configuring valve assembly 72 such that there is, in essence, a small leak from the side of the valve coupled to the pressure generator, i.e., chamber 134 in FIG. 7B. This bleed off leak is provided according to one embodiment of the present invention by providing a clearance between inner cylinder 80 (more specifically, second barrel 86 of inner cylinder 80) and outer cylinder 100. This clearance is sized so as to allow a bleed off flow of gas from chamber 134 even if the blower discharge slot 92 is completely blocked by outer cylinder 100. Such a bleed off flow has an additional benefit in that it provides an air bearing for the outer cylinder over the inner cylinder thereby reducing the friction between these two cylinders. However, such a bleed off flow does not provide the cooling benefit of the flow from port 76 in FIG. 4.

The present invention also contemplates that the bleed off leak from chamber 134 can be achieved by providing a hole through separation plate 96 that allows a small amount of bleed off flow from chamber 134 to chamber 136 on the opposite side of the separation plate. Chamber 136 is preferably coupled to first conduit 62 as discussed above with respect to FIG. 4.

The invention has been described with reference to the preferred embodiments. Obvious modifications and alterations will occur to others upon reading and understanding the preceding detailed description. For example, other configurations of inner cylinder 80, outer cylinder 100, the slots defined in these cylinders, magnet 98 and coil 104 are contemplated. For example, magnet 98 and coil 104 can be reversed so that the magnet is provided on the outer cylinder and the coil is provided on the inner cylinder. It is intended that the invention be construed as including all such modifications and alterations insofar as they come within the scope of the appended claims or the equivalents thereof.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A valve assembly comprising:
a first hollow member having an open first end, an open second end, a blower discharge opening defined by at least a portion of a wall thereof, an exhaust intake opening defined by at least a portion of the wall thereof between the blower discharge opening and the second end, and a separating member disposed in the first hollow member between the blower discharge opening and the exhaust intake opening;
a second hollow member having a first opening defined by at least a portion of a wall thereof, with the second hollow member positioned coaxially around the first hollow member; and
an actuator associated with the first hollow member and the second hollow member for moving the second hollow member with respect to the first hollow member.

2. A valve assembly according to claim 1, wherein the actuator comprises:
a magnet secured to one of the first hollow member and the second hollow member; and
a coil secured around the other of the first hollow member and the second hollow member in magnetic flux coupled relation with the magnet and configured to receive DC current.

3. A valve assembly according to claim 1, wherein:
the first hollow member includes a center barrel, a first barrel, and a second barrel, with the first barrel and the second barrel positioned coaxially at opposite ends of the center barrel;
the magnet is mated with the center barrel;
the second hollow member has the coil received therearound;
the second hollow member is received in sliding engagement around the magnet and the center barrel with the first opening of the second hollow member positioned at the end of the first hollow member adjacent the second barrel; and
the second barrel includes the blower discharge opening, the exhaust discharge opening, and the separating member, with the second barrel having one end received in the end of the second hollow member opposite the first barrel and secured to the end of the center barrel.

4. A valve assembly according to claim 1, wherein the magnet and coil are configured and arranged such that in response to receiving DC current of a first polarity, the coil urges the second hollow member axially relative to the first hollow member so that the first opening of the second hollow member and the blower discharge opening of the first hollow member overlap, and so that in response to receiving DC current of a second polarity, opposite the first polarity, the coil urges the second hollow member axially relative to the first hollow member so that the first opening of the second hollow member and the exhaust intake opening of the first hollow member overlap.

5. A valve assembly according to claim 1, wherein the first hollow member has stops at opposite ends thereof that coact with ends of the second hollow member to restrict axial movement of the second hollow member between the ends of the first hollow member.

6. A valve assembly according to claim 5, wherein at least one stop at an end of the first hollow member is comprised of a shoulder formed therearound.

7. A valve assembly according to claim 1, wherein at least a portion of at least one of the blower discharge opening and the exhaust intake opening is defined in the first hollow member in one of a diagonal, circular, arched and a spiral configuration.

8. A valve assembly according to claim 1, wherein at least one of the blower discharge opening, the exhaust discharge opening, and the first opening is shaped to so as to have a varying mechanical gain.

9. A valve assembly according to claim 1, wherein during operation, the blower discharge opening overlaps the first opening provided in the second hollow member to define an aperture in the valve assembly, wherein movement of the second hollow member relative to the first hollow member changes the size of the aperture.

10. A valve assembly according to claim 1, wherein during operation of the pressure support system, the exhaust discharge opening overlaps the first opening provided in the second hollow member to define an exhaust aperture in the valve assembly, wherein movement of the second hollow member relative to the first hollow member changes the size of the exhaust aperture.

11. A valve assembly according to claim 1, wherein during operation of the pressure support system, both the blower discharge opening and the exhaust discharge opening overlap the first opening provided in the second hollow member, wherein overlap of the blower discharge opening and the first opening define a first aperture in the valve assembly and overlap of the exhaust discharge opening and the first opening define a second aperture in the valve assembly, wherein movement of the second hollow member relative to the first hollow member simultaneously changes the size of the first aperture and the second aperture.

12. A valve assembly according to claim 1, wherein a clearance is provided between the first hollow member and the second hollow member sufficient to provide a continuous flow of gas therethrough.

13. A pressure support system comprising:
a pressure generator having an inlet portion and an outlet portion for generating a flow of gas;
a first conduit having a first end open to ambient atmosphere and a second end coupled to the inlet portion of the pressure generator to supply gas from a gas source to the pressure generator;
a second conduit having a first end coupled to the outlet portion of the pressure generator and a second end to deliver the flow of gas from the pressure generator to a patient; and
a valve assembly operatively connected to the second conduit to control one of a pressure and a rate of the flow of gas in the second conduit, wherein the valve assembly comprises:
a first hollow member having an open first end, an open second end, a blower discharge opening defined by at least a portion of a wall thereof, an exhaust intake opening defined by at least a portion of the wall thereof between the blower discharge opening and the second end, and a separating member disposed in the first hollow member between the blower discharge opening and the exhaust intake opening, a second hollow member having a first opening defined by at least a portion of a wall thereof, with the second hollow member positioned coaxially around the first hollow member, and an actuator associated with the first hollow member and the second hollow member for moving the second hollow member with respect to the first hollow member.

14. A pressure support system according to claim 13, further comprising a port defined in the second conduit for directing a portion of the flow of gas from the second conduit for cooling purposes.

15. A pressure support system according to claim 13, further including:

a pressure sensor that measures fluid pressure in the second conduit and produces a pressure signal indicative thereof;

a flow sensor that measures fluid flow in the second conduit and produces a flow signal indicative thereof; and a controller operatively coupled to the pressure sensor and the fluid sensor and to the valve assembly, wherein the controller actuates the valve assembly to control one of a pressure and a rate of the flow of gas in the second conduit.

16. A pressure support system according to claim 13, wherein a clearance is provided between the first hollow member and the second hollow member sufficient to provide a continuous flow of gas therethrough from the pressure generator.

17. A pressure support system according to claim 13, wherein at least one of the blower discharge opening, the exhaust discharge opening, and the first opening is shaped to so as to have a varying mechanical gain.

* * * * *